United States Patent
Yang

(10) Patent No.: US 8,802,430 B2
(45) Date of Patent: Aug. 12, 2014

(54) MICRO AND NANO GLASS BALLS EMBEDDED IN A GEL PRESENTING MICROMETER AND NANOMETER SCALE CURVATURE AND STIFFNESS PATTERNS FOR USE IN CELL AND TISSUE CULTURING AND A METHOD FOR MAKING SAME

(71) Applicant: Shengyuan Yang, West Melbourne, FL (US)

(72) Inventor: Shengyuan Yang, West Melbourne, FL (US)

( * ) Notice: Subject to any disclaimer, the term of this patent is extended or adjusted under 35 U.S.C. 154(b) by 0 days.

(21) Appl. No.: 13/656,808

(22) Filed: Nov. 25, 2012

(65) Prior Publication Data
US 2014/0147918 A1 May 29, 2014

(51) Int. Cl.
*C12N 5/00* (2006.01)

(52) U.S. Cl.
USPC .......................... 435/325; 435/403; 435/397

(58) Field of Classification Search
CPC ....... A61K 38/00; A61K 39/00; C07K 14/47; C07K 2319/00; C07K 14/705
USPC .................... 435/357, 325, 403, 397
See application file for complete search history.

(56) References Cited

U.S. PATENT DOCUMENTS

2009/0197333 A1* 8/2009 Saito et al. .................... 435/377
2010/0129908 A1* 5/2010 Fang et al. .................... 435/370

OTHER PUBLICATIONS

Hwang et al., Controlled cellular orientation on PLGA microfibers with defined diameters, Biomed Microdevices (2009) 11:739-746.*
James et al., Subcellular Curvature at the Perimeter of Micropatterned Cells Influences Lamellipodial Distribution and Cell Polarity, Cell Motility and the Cytoskeleton 65: 841-852 (2008).*
Rumpler et al., The effect of geometry on three-dimensional tissue growth, J. R. Soc. Interface (2008) 5, pp. 1173-1180.*
Smeal et al., Substrate Curvature Influences the Direction of Nerve Outgrowth, Annals of Biomedical Engineering, vol. 33, No. 3, Mar. 2005, pp. 376-382.*
Kang et al., Porous Poly(Lactic-Co-Glycolic Acid) Microsphere as Cell Culture Substrate and Cell Transplantation Vehicle for Adipose Tissue Engineering, Tissue Engineering: Part C vol. 14, No. 1, 2008.*
Wang, et al, "Preparation of a Flexible, Porous Polyacrylamide Substrate for Mechanical Studies of Cultured Cells", Methods in Enzymology, vol. 298, p. 489-496, 1998.

* cited by examiner

*Primary Examiner* — Karen Cochrane Carlson
*Assistant Examiner* — Jennifer M. H. Tichy
(74) *Attorney, Agent, or Firm* — John L. DeAngelis; Beusse Wolter Sanks & Maire, P.A.

(57) ABSTRACT

A substrate for use in culturing cells or tissues. The substrate comprises a gel, one or more microstructures partially embedded within a surface of the gel, the one or more microstructures presenting two different curvatures or presenting two different stiffness values or presenting a combination of different curvatures and different stiffness values, wherein the microstructures are disposed at defined locations within the surface of the gel, and wherein the cells and tissues are cultured on an exposed surface of the microstructures.

18 Claims, 1 Drawing Sheet

MICRO AND NANO GLASS BALLS EMBEDDED IN A GEL PRESENTING MICROMETER AND NANOMETER SCALE CURVATURE AND STIFFNESS PATTERNS FOR USE IN CELL AND TISSUE CULTURING AND A METHOD FOR MAKING SAME

REFERENCE TO RELATED APPLICATIONS

The present application is a continuation in part of application Ser. No. 13/426,593 filed on Mar. 21, 2012, which is incorporated by reference herein in its entirety.

FIELD OF THE INVENTION

The present invention is directed generally to micro glass balls embedded in gels and more particularly to such micro glass balls embedded in gels for use in studying cell and tissue mechanobiological responses to curvature and stiffness patterns in a substrate.

BACKGROUND OF THE INVENTION

Cells survive in a mechanical environment of a tissue that the cells are part of. It has been shown that cell behaviors are extremely sensitive to the stiffness of the substrate on which the cells grow. For example, cell growth and movement can be guided solely by the rigidity or stiffness of the substrates: epithelial cell traction forces are proportional to substrate rigidity; matrix elasticity directs stem cell lineage specification; on microstructured anisotropic substrates, epithelial cells migrate along the direction of greatest stiffness; within a range of stiffness values spanning that of soft tissues, fibroblasts tune their internal stiffness to match that of their substrate.

Studies of interactions between cells and their surrounding environments have been receiving increased attention over the past twenty years. The results of several such studies are summarized below. Cell-substrate interactions can profoundly affect cell behavior, including adhesion, spreading, migration, division, differentiation, and internal cellular signaling. The binding interactions between cells and their substrate(s) are influenced by mechanical stimuli such as substrate stiffness and substrate curvatures. The effects of substrate stiffness on cell behaviors have been extensively studied. However, the effects of substrate curvature are not well documented. Since the substrates of cells in vivo are normally not flat, the responses of cells to substrate curvatures should also be a fundamental aspect of cell mechanosensitivity and mechanotransduction to its substrates. The importance of substrate curvature effects on cell behaviors can be illustrated by understanding the process of cell attachment and growth on curved surfaces of bones and implants in vivo.

Researchers use the term "contact guidance" to describe the orientation of cell locomotion in response to the topographic structures of the substrates. In 1976, by culturing chick heart fibroblasts on convex cylindrical glass fibers, researchers Dunn and Heath demonstrated that cells respond to substrate curvatures when the radii of the substrate curvatures are comparable to the cell sizes, and they fitted a radius of curvature of 100 µm above which the curvature effects on cell behavior were negligible.

Dunn and Ebendal showed that contact guidance on aligned collagen gels is largely a response to the three-dimensional shape of the substrate. By comparing normal and virally transformed hamster cells, Fisher and Tickle illustrated that the organization of microfilaments plays a role in determining the orientation of cells on curved surfaces.

Smeal et al., determined that substrate curvature was sufficient to influence the directional outgrowth of nerve cells by culturing nerve cells on filamentous surfaces and measuring directional growth. They found that the mean direction of neurite outgrowth aligned with the direction of minimum principal curvature, and the spatial variance in outgrowth direction was directly related to the maximum principal curvature. Maduram et al. established a dependence between cell polarity and shape by noting the presence of small molecules that alter actomyosin contractility. This finding revealed a stronger dependence on contractility for shapes having straight edges in contrast to those having curved edges.

Rumpler et al. investigated the role of substrate curvature on the growth of tissues. They reported that the local rate of the tissue formed by osteoblasts is strongly influenced by the geometrical features of the channels in an artificial three-dimensional matrix. Curvature-driven effects and mechanical forces within the tissue explained the growth patterns as demonstrated by numerical simulation and confocal laser scanning microscopy. Hwang et al. investigated the effects of microfiber diameter on the orientation of adhered cells. For this purpose, mouse fibroblast L929 cells were cultured on the surface of poly(D,L-lactic-co-glycolic acid) (PLGA) fibers of defined diameters ranging from 10 to 242 µm, and their adhesion and alignment were quantitatively analyzed. They found that the mean orientation of cells and the spatial variation of the cell alignment angle directly related to the microfiber diameter. Cells cultured on microfibrous scaffolds oriented along the long axis of the microfiber. An increase in cellular orientation along the longitudinal direction was noted as fiber diameter decreased.

Sanz-Herrera et al. proposed a cell constitutive model to mathematically simulate cell attachment on curved substrates, activated by contractile forces. They analyzed a single fiber bundle composed of microtubules and actin filaments activated by actomyosin motors. Then the model was macroscopically extended to the cytoskeletal level using homogenization.

In the above-mentioned literature, substrate curvature effects on cell behaviors were studied by experiments using glass rods or polymer fibers. To date, there is no reported experimental study on curvature effects of spherical substrates on cell behaviors, which motivated research by the present inventor and lead to the development of the described invention.

BRIEF DESCRIPTION OF THE DRAWINGS

The features of this invention will be apparent from the following description of the invention, as illustrated in the accompanying drawings, in which like reference characters refer to the same parts throughout the different figures.

DETAILED DESCRIPTION OF THE INVENTION

Figure 1:
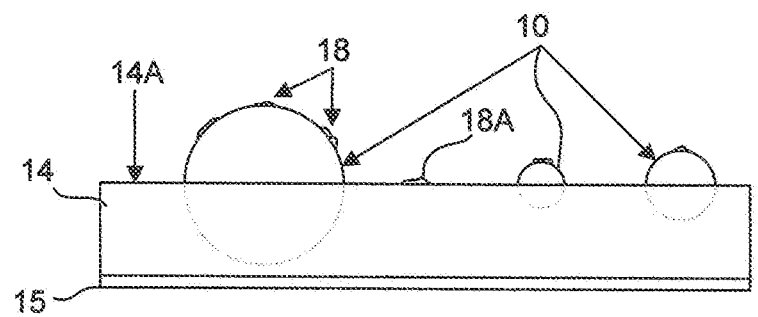
FIGS. 1, 2, 3 and 4 illustrate various embodiments of microstructures for use in culturing cells and tissues according to the present invention.

Before describing in detail the particular micro glass ball embedded gels in accordance with the present invention and methods for making same, it should be observed that the present invention resides primarily in a novel combination of elements and method steps. Accordingly, these elements have been represented by conventional elements in the drawings, showing only those specific details that are pertinent to the present invention so as not to obscure the disclosure with structural details that will be readily apparent to those skilled in the art having the benefit of the description herein.

The following embodiments are not intended to define limits as to the structure or methods of the invention but only to provide exemplary constructions. The described embodiments are permissive rather than mandatory and illustrative rather than exhaustive.

The present invention introduces teaches polyacrylamide (PA) gels embedded with micro glass balls (also referred to a microstructures) of various diameters to study cell mechanobiological responses to substrate curvatures. In one application the inventor cultured NIH-3T3 mouse fibroblasts on glass balls having diameters ranging from 5 µm to 2 mm, and analyzed the cell morphologies by using an optical microscope and a 3D confocal laser scanning microscope. The inventor found that the fibroblasts are sensitive to the curvatures of the balls, and there are significant differences in the attachment rates, migration speeds, and morphologies for cells cultured on glass balls of diameters at or below about 500 µm. The inventor also observed the cell spreading responses to the local stiffness effect of the glass balls, and compared the cell migration behavior on cylindrical glass tubes with similar diameters to the glass balls.

Although the present application refers to balls, spheres and cylinder shapes (i.e., microstructure) on which the cells are cultured, other shapes can also be employed; that is, curves on an exposed surface of the structures can be controlled to provide certain radii or the structures can be formed to provide random curves and/or random shapes. Certain structural shapes are described in the related patent application referred to above, i.e., application Ser. No. 13/426,593.

The microstructures can range in size from about 5 µm to about 2 mm as described herein, presenting micro- and nano-interfaces between the substrate and the cells.

The shaped microstructures, whether all having the same shape or different shapes and whether all have the same size or different sizes and the same stiffness or different stiffness values, can be disposed within the gel to provide various shapes and stiffness patterns for cell and tissue culturing. The stiffness patterns and shapes can be predetermined by an ordered placement (e.g., uniform, periodic or symmetrical) of the structures or the structures can be randomly distributed within the gel to provide a random shapes and stiffness patterns. Both the ordered and random placement of the stiffness values and structure shapes and sizes within the gel are important for use in cell and tissue culturing.

In another embodiment the shaped structures present different stiffness values and these structures can be used in cell and tissue culturing experiments. Such substrates can be referred to as micro- and nano-composites materials.

A material of the variously shaped structures comprises glass or any composite materials that will permit the culturing of cells thereon. Also, all the structures (i.e., regions having certain stiffness values) used in any one cell culturing experiment do not need to comprise the same material.

Substrate Preparation

The protocol used to prepare the PA gels is described below. According to one embodiment a 40% w/v (weight/volume) acrylamide stock solution is prepared by mixing 40 g of acrylamide powder (available from Fisher-Biotech, Pittsburgh, Pa., CAS no. 79061) with 100 mL of deionized $H_2O$. A 2% w/v bis-acrylamide stock solution is prepared by mixing 1 g bis-acrylamide powder (available from Fisher-Biotech, Pittsburgh, Pa., CAS no. 110269) with 50 mL deionized $H_2O$. Final volumes of 1000 µl of PA solutions are prepared by mixing the acrylamide stock solution at final concentrations of 3% to 8% w/v with the bis-acrylamide stock solution at final concentration of 0.02% to 0.1% w/v. To polymerize the PA solutions, 1.5 µL of N,N,N,N-tetramethylethylenediamine (TEMED) (available from Fisher-Biotech, Pittsburgh, Pa., CAS no. 110189) and 5 µL of 10% w/v ammonium persulfate are added to the mixed PA solutions.

A fixed volume of 100 µL of the PA solution is pipetted onto the center of a 30 mm-diameter cell culture dish. Depending on the desired studies, appropriate numbers or a combination of glass balls with diameters of about 2 mm, 1.1 mm, 900 µm, 750 µm, 500 µm, mixed 50-300 µm, and mixed 5-100 µm (available from Blockheadstamps of Portland, Oreg.) are immediately dropped onto the PA solution. To evenly press the glass balls into the unpolymerized gel, a 22 mm-diameter cover slip is then carefully placed on top of the PA solution. The polymerization process is completed in about 24 hours and then the top cover slip is slowly peeled off. The glass ball embedded PA gel, which is attached to the cell culture dish, is soaked with 5 ml PBS for about three days.

PA gels with a wide range of elastic moduli, E, can be prepared using the concentration scheme described above. The most flexible gel with 3% w/v acrylamide and 0.10% w/v bis-acrylamide has an elastic modulus (E) of 1 kPa, while the stiffest gel with 8% w/v acrylamide and 0.08% w/v bis-acrylamide yields an E of 75 kPa. In addition, the intermediate gel with 8% w/v acrylamide and 0.02% w/v bisacrylamide has an E of 10 kPa.

Since cultured cells adhere poorly to the PA surface, the inventor coated the gels with adhesion molecules to provide a physiological adhesive surface for the cell culture. The inventor coated a Fibronectin-like engineering protein (available from Sigma-Aldrich of St. Louis, Mo., no. F8141-1MG) on the glass ball embedded PA gel surface and then these gels were left at room temperature for about 24 hours before plating cells.

In addition, the inventor also prepared cylindrical glass tubes (available from Fisher Scientific of Atlanta, Ga., No. 212011A) having diameters similar the diameters of the glass balls. In one embodiment the diameters of the cylindrical glass tubes are 2 mm, 1.09 mm, 930 µm, 760 µm, 530 µm, and 460 µm. Both ends of the cylindrical glass tubes are fixed on the bottom of cell culture dish by using 75 kPa PA gels to prevent any sliding or rolling of the cylindrical glass tubes.

Cell Culturing

NIH-3T3 mouse fibroblasts were cultured in Dulbecco's Modified Eagle Medium (available from ATCC of Manassas, Va., no. 30-2002) with 4500 mg/L glucose, 4 mM L-glutamine, 1 mM sodium pyruvate, and 1500 mg/L sodium bicarbonate, 10% calf bovine serum (available from ATCC of Manassas, Va., No. 30-2030), and 1% penicillin-streptomycin (available from MP Biomedicals of Solon, Ohio, No. 091670049). The cells were incubated at 37° C. with a humidified 5% $CO_2$ atmosphere and the culture medium was changed twice per week.

Cell Staining and Confocal Microscopy

To obtain three-dimensional (3D) images of cells on curved surfaces, the inventor used a confocal laser scanning microscope (available from Nikon Instruments Inc. of Melville, N.Y., Eclipse 90i). For confocal microscopy, the cells were directly treated using a membrane probe, N-(3-Triethylammoniumpropyl)-4-(4-(Dibutylamino)styryl) Pyridinium Dibromide (available from FM of Carlsbad, Calif., 1-43 invitrogen no. T3163), through 5 µg/ml diluted in ice-cold Hanks' balanced salt solution (HBSS) (available from Invitrogen of Carlsbad, Calif., no. 14175079).

A. Glass Ball Embedded PA Gel Platform

A class of PA gels with glass balls embedded with diameters of 2 mm, 1.1 mm, 900 µm, 750 µm, 500 µm, mixed 50-300 µm, and mixed 5-100 µm were prepared by using the protocol described above. FIG. 1 illustrates microstructures 10 embedded in a PA gel platform 14 for use in tissue and cell culturing. The PA gel platform is disposed on a material sheet 15. In this platform, some cells 18 reside on the top of the microstructures 10 while other cells 18A live on a surface 14A of the PA gel platform 14.

The extent to which the microstructures are embedded in the gel can be randomly determined, for example, by simply dropping the microstructures onto an exposed surface of the gel. In another embodiment the microstructures can be disposed such that an equal volume of each microstructure extends above the surface 14A or each microstructure extends an equal distance above the gel surface 14A.

The gel platform 14 functions as both a soft substrate and an adhesive surface to prevent any sliding or rolling of the glass balls 10. As can be seen in a scanning electron microscope (SEM) image of this platform (not shown) with glass balls of 900 µm-, 500 µm-, and below 300 µm-diameters extending out from an upper surface of the PA gel platform 14. Because microstructures float on top of the PA gel solution prior to polymerization, the tops of the microstructures may be bare or have a thin coating of the PA gel material.

Figure 2:
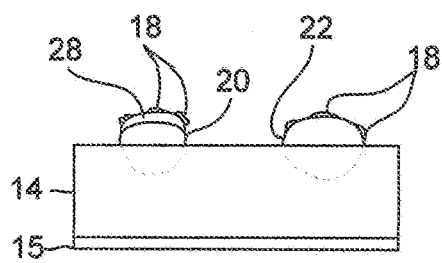

FIG. 2 illustrates microstructures 20 and 22 disposed in the PA gel platform 14. An additional layer of gel material 28 is disposed on the microstructure 20 and the cells 18 grow on the gel material 28. The cells 18 grow directly on the microstructure 22 with no intervening layer of gel material.

Figure 3:
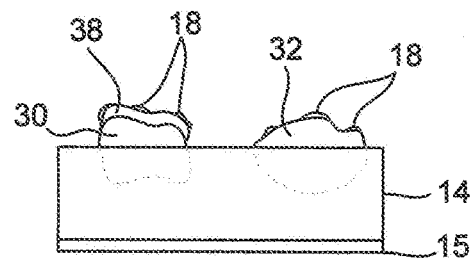
Figure 4:
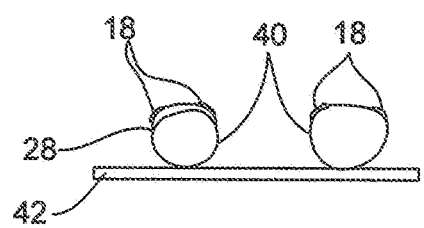

FIG. 3 illustrates microstructures 30 and 32 disposed in the PA gel platform 14. An additional layer of gel material 38 is disposed on the microstructure 30 and the cells 18 grow on the gel material 38. The cells 18 grow directly on the microstructure 32 with no intervening layer of gel material FIG. 4 illustrates an embodiment without the gel platform layer. In this embodiment the microstructures 40 are disposed on a material layer 42. An adhesive material (not shown) affixes the microstructures 40 to the material layer 42.

The inventor has compared the cells cultured on the PA gel material, cells cultured on the glass ball microstructures with a thin coating of PA gel material, and cells cultured on bare glass ball microstructures. He has determined that the cells cultured on these three surfaces have different morphologies. Within 24 hours in culture, cells on bare glass balls formed a few long narrow lamellipodia to spread and migrate, but cells on PA gels and cells on glass balls with a thin coating of PA did not form lamellipodia.

The surfaces of the glass balls may not be smooth. In one embodiment the 150 µm- and 500 µm-diameter glass balls were less rough than the 2 mm-diameter glass ball. It has been shown that nano-scale surface roughness affects cell morphology, proliferation, and immunophenotype. However, here the inventor did not consider the effect of nano-scale topography.

Effects of Substrate Curvature on Fibroblast Morphology

After 24 hour in culture, the NIH-3T3 fibroblasts on the 2 mm-diameter glass ball were very well spread. These fibroblasts were almost indistinguishable from those grown on flat glass. The cells on both the flat glass and 2 mm-diameter glass ball were very well spread and had two or three lamellipodia for active migration. Also, for both surfaces, the formation of some small clusters of cells was noted. This means the cells migrated actively to connect with each other and cellular division began occurring at this time. The cells on the 2 mm-diameter glass ball were slightly less spread than the cells on the flat glass although both the cells on the flat glass and the cells on the 2 mm-diameter glass ball had similar morphologies and behaviors. It was evident that the cells can recognize large radii of curvature such as 2 mm-diameter glass balls.

The cells on the 1.1 mm-, 900 µm-, and 750 µm-diameter glass balls had the similar cell shapes. The cells were less spread compared to those on the flat glass and 2 mm-diameter glass ball. While some cells still had a round shape with two short lamellipodia after 24 hours in culture, the majority of the cells had a more spread shape.

On the other hand, the cells on a 500 µm-diameter glass ball had different cell shapes compared to the cells on larger balls. The round cells were dominant and some cells formed a long narrow lamellipodium while still being round. Although these cells did not spread and migrate actively, the inventor observed that they grew minimally and stayed round after 48 hours in culture.

The cells placed on the 154 µm- and 68 µm-diameter glass balls closely resembled the cells on the 500 µm-diameter glass ball, which were round-shaped with one or two lamellipodia.

Confocal Laser Scanning Microscopy

Confocal microscope images of two NIH-3T3 fibroblasts on a flat glass and on a 900 µm-diameter glass ball were also recorded. The fibroblast on the flat glass was very well spread and had many filopodia. The height of this fibroblast was measured to be 8 µm along a YZ axis view. The fibroblast maintained a round shape with two long narrow lamellipodia.

Cell Spreading Behaviors Due to the Effect of Local Substrate Stiffness

It is well known by those skilled in the art that cell spreading depends on substrate stiffness. Cells generate more traction force and develop a broader and flatter morphology on stiffer substrates than they do on softer but equally adhesive substrates. Cells preferentially migrate from a soft to a hard surface. Normal NIH-3T3 cells, for instance, undergo more apoptosis and less proliferation on soft as opposed to stiff substrates. Most cell types studied spread more and adhere better to harder substrates, and some cannot grow on very soft (<50 Pa) surfaces. In the inventor's experiments, he found that on the 75 kPa pure PA gels, NIH-3T3 cells spread well and migrated actively. The inventor made 75 kPa gels embedded with diameters of mixed 5-100 µm microstructures or glass balls. A round cell was formed on two glass balls with the cell wrapped over the two glass balls. This cell grew and spread over the two glass balls. Cells placed on very small glass balls with diameters smaller than about 20 µm did not spread and migrate. They maintained a round shape while growing on the balls and then similarly wrapped over the small glass balls. They also lived on the balls because the glass balls were stiffer than the 75 kPa gel. It was observed that cells on the 75 kPa gel were still moving actively while cells on the small glass balls were still wrapped over the glass ball after 96 hours in culture.

The inventor also found NIH-3T3 fibroblasts cannot attach and spread on 10 kPa PA gels. Even when the inventor attached cells on the surface of the 10 kPa gels with fibronectin coating, the attached cells still did not spread. However, fibroblasts could spread when there were very small stiff particles near the cells. Some cells stretched over two small glass balls with diameters smaller than 30 µm, while other cells located on the surface of the 10 kPa gel were still round. The cell extended two lamellipodia to the glass balls and the ends of the two lamellipodia stuck to the two glass balls, respectively. This observation shows that the cell spreading behaviors respond to local substrate stiffness.

Cell Migration on Both Spherical and Cylindrical Surfaces

The inventor observed cell migration behaviors on both the glass balls and the cylindrical glass tubes with various diameters. Cell movements on a glass ball with a diameter of 500 μm and movements on a cylindrical glass tube with a diameter of 440 μm were observed. On the glass ball, a round cell with two long narrow lamellipodia migrated without directivity on the surface of the ball for 48 hours in culture. On the cylindrical glass tube, after 6 hours in culture, a narrow and long fibroblast was observed on the center surface of the glass tube angled at about 45° to the longitudinal direction of the glass tube. After 12 hours in culture, this cell shortened in length and rotated by about 10° to the longitudinal direction of the tube. This cell shortened again and aligned itself parallel to the longitudinal direction of the tube after 24 hours in culture. This fibroblast became round and moved in the opposite direction after 48 hours in culture. Therefore, the cell on the cylindrical glass tube tended to align to the longitudinal direction of the tube while the cell on the glass ball migrated irregularly. Both of the cells showed poor motilities and growth rates for 48 hours in culture.

The cell spread area was measured for a number of randomly selected cells ($n_{total}=95$). In general, the mean cell spread area decreased with the decreasing of the glass ball diameter, from flat glass plates to large balls to small balls. The smallest cell spread area, 209 μm², was found on a 63 μm-diameter glass ball, and the maximal average cell spread area, 1592 μm², was clearly obtained with flat glass plates. The smallest glass ball to which a fibroblast adhered without wrapping over the glass ball was 58 μm in diameter. The cell spread area increased as a function of the ball diameter with three different slopes in the three distinct regions depending on the ball diameters. In a Region 1 cells grew on 50-300 μm-diameter glass balls, and the cell spread area, as a function of the ball diameter, fitted a linear relationship ($n_{Region\ 1}=35$) with the largest slope compared to those of Region 2 and Region 3. In Region 2, cells grew on 500-900 μm-diameter glass balls, the mean cell spread area had a linear trend ($n_{Region\ 2}=30$) as a function of the ball diameter, but the slope was approximately 24% of the slope for Region 1. In Region 3, cells grew on 1.1 mm-diameter glass balls, 2 mm-diameter glass balls, and to flat glass, the mean cell spread area increased with the increase of the ball diameter, and the slope between data points of the 1.1 mm-diameter glass balls and 2 mm-diameter glass balls was similar to that of Region 2 ($n_{Region\ 3}=30$). From 900 μm-diameter to 1.1 mm-diameter glass balls, there was a 50% sudden rise in the mean cell spread area. The mean comparison of one-way analysis of variance (ANOVA) with the Tukey and Dunnett C post-test indicated that the mean cell spread area for each diameter of the glass balls significantly differ from each other at the 0.01 level of significance.

The fibroblasts showed lower attachment rates and migration speeds when the diameter of the glass balls decreased. For glass balls of diameters at or below 500 μm, the fibroblasts had very low attachment rates and migration speeds for larger glass balls. Thus, although the fibroblasts can easily attach the surfaces of glass balls with large radii, such as flat glass plates and 2 mm-diameter glass balls, it is hard for them to adhere to the surfaces of glass balls with small radii or curvatures, such as below 500 μm-diameter glass balls. In addition, the cells growing on glass balls of diameters at or below 500 μm showed higher aspect ratios compared to those growing on glass balls of larger diameters. Therefore, the inventor concluded that the attachment, spreading, migration behaviors of the NIH-3T3 fibroblasts are sensitive to the substrate curvatures and these behaviors for cells growing on substrates with diameters at or below 500 μm are significantly different from those for cells growing on substrates with larger diameters.

In summary, micro glass ball (microstructures) embedded PA gels were developed to study cell mechanobiological responses to substrate curvatures. NIH-3T3 mouse fibroblasts were cultured on these substrates with glass balls ranging in diameters from 5 μm to 2 mm, and morphologies of cells growing on glass balls were analyzed by an optical microscope and a 3D confocal laser scanning microscope. The curvature of the surface to which a cell adheres has profound effects on cell attachment, migration, and morphology. Fibroblasts showed lower spread areas and migration speeds as the diameter of the glass ball decreased, and showed poor growth rates and motilities both on glass balls and on cylindrical glass tubes with diameters at or less than 500 μm. Cell spreading behavior responded to the local stiffness effect induced by the glass balls in the gels. Experiments showed that the cells did not spread on a stiff gel but wrapped over the small glass balls, and the cells spread on a soft gel by attaching to the two small separate glass balls. When a cell attaches to a curved surface, it creates a distortion on the cell cytoskeleton, and then the cell does not work in an optimal position since the actin filaments in the cell cytoskeleton are misaligned and separated from the flat surface. Therefore, it is necessary to measure the cell adhesion forces on the curved surfaces of bones and implants in vivo by using traditional methods as well as novel bio micro and nano electro mechanical systems (bio MEMS/NEMS) force sensors. The studies of substrate curvature effects on other cell behaviors will play fundamental roles in cell and tissue engineering. The cell culture experiments and related discussions reported here imply that this class of substrates, micro glass ball embedded gels, can be useful tools to study cell mechanobiological responses to substrate curvatures, related cell and tissue engineering researches, and biomedical applications.

Applications of the present invention are many, including for use in general cell studies as described herein, wherein the invention allows control over the morphology and structure of the resulting cells and tissues. Also, stem cells can be cultured on substrates formed according to the teachings of the present invention. It has been shown that the degree of curvature influences differentiation and lineage of these stem cells. Early detection and isolation of cancer cells can also be accomplished using the teachings of the present invention, which may lead to new strategies and devices for cancer detection.

Parent application Ser. No. 13/426,593 describes and claims a high stiffness frame. The location and size of the openings within that frame can be varied and need not be uniform. According to the present invention, one or more glass balls or microstructures can be disposed within each frame opening.

It is to be understood that the above-described arrangements are merely illustrative of the many possible specific embodiments that can be devised to represent application of the principles of the invention. Numerous and varied other arrangements can be devised in accordance with these principles by those skilled in the art without departing from the spirit and scope of the invention.

What is claimed is:

1. A substrate for use in culturing cells and tissues, the substrate comprising:
   a material sheet;
   a gel disposed above the material sheet;
   microstructure particles partially embedded and immovable within the gel and not attached to the material sheet, a portion of each microstructure particle protruding above a surface of the gel and presenting one or more curved surfaces above the surface of the gel, the curved surfaces comprising indentations and protrusions;

wherein the surface of the gel comprises an adhesive surface to prevent motion of the microstructures particles relative to the gel;

the gel and the microstructure particles comprising different materials; and the substrate for use in culturing cells and tissues on an exposed surface of the microstructure particles.

2. The substrate of claim 1 wherein the gel comprises polyacrylamide gel.

3. The substrate of claim 1 wherein the surface of the gel has a curved or a planar shape.

4. The substrate of claim 1 wherein a shape of the microstructures particles comprises one of a sphere, a cylinder and an oval.

5. The substrate of claim 1 wherein a material of the microstructures particles comprises glass or a composite material.

6. The substrate of claim 1 wherein a diameter of the microstructures particles is between about 5 µm and about 2 mm.

7. The substrate of claim 1 wherein the microstructures particles present different stiffness values.

8. The substrate of claim 1 further comprising adhesion molecules on a surface of the microstructures particles and wherein the cells and tissues are cultured on the adhesion molecules.

9. The substrate of claim 8 wherein the adhesion molecule comprises a Fibronectin-like engineering protein.

10. The substrate of claim 1 further comprising an additional gel disposed on a surface of the microstructures particles and wherein the cells and tissues are cultured on the additional gel.

11. The substrate of claim 1 further comprising a layer of gel on a surface of a first microstructure particle, a second microstructure embedded in the layer of gel on the surface of the first microstructure particle.

12. The substrate of claim 1 wherein the microstructure particles are disposed at defined locations within the surface of the gel, the defined locations comprise a defined distance between at least two microstructures particles.

13. A substrate for use in culturing cells or tissues, the substrate comprising:

a material sheet;

a gel above the material sheet;

microstructures particles partially embedded and immoveable within the gel and not attached to the material sheet, a portion of a microstructure particle protruding above a surface of the gel and presenting one or more curved surfaces above the surface of the gel, the curved surfaces comprising indentations and protrusions;

wherein the surface of the gel comprises an adhesive surface to prevent motion of the microstructures particles relative to the exposed gel; and wherein the microstructures particles are disposed at random locations within the surface of the gel;

the gel and the microstructure particles comprising different materials; and the substrate for use in culturing cells and tissues on an exposed surface of the microstructure particles.

14. The substrate of claim 13 wherein the gel comprises polyacrylamide gel.

15. The substrate of claim 13 wherein the surface of the gel has a curved or a planar shape.

16. The substrate of claim 13 wherein a shape of the microstructures particles comprises one of a sphere, a cylinder and an oval.

17. The substrate of claim 13 wherein a material of the microstructures particles comprises glass or a composite material.

18. The substrate of claim 13 wherein a diameter of the microstructures particles is between about 5 µm and about 2 mm.

* * * * *

UNITED STATES PATENT AND TRADEMARK OFFICE
CERTIFICATE OF CORRECTION

PATENT NO. : 8,802,430 B2
APPLICATION NO. : 13/656808
DATED : August 12, 2014
INVENTOR(S) : Shengyuan Yang It is certified that error appears in the above-identified patent and that said Letters Patent is hereby corrected as shown below:

In the Specification

Column 8, Lines 42-43, the statement "It has been shown that the degree of curvature influences differentiation and lineage of these stem cells" should be DELETED.

Signed and Sealed this
Twenty-eighth Day of April, 2020

Andrei Iancu
*Director of the United States Patent and Trademark Office*